United States Patent [19]

Kawai et al.

[11] Patent Number: 4,617,104
[45] Date of Patent: Oct. 14, 1986

[54] CELL UNIT FOR OBSERVING ELECTROPHORESIS

[75] Inventors: Yoshio Kawai, Musashino; Kiyoshi Kitagawa, Komae; Kazue Endo, Kashiwa; Chikau Onodera, Urawa, all of Japan

[73] Assignee: Kureha Kagaku Kogyo Kabushiki Kaisha, Tokyo, Japan

[21] Appl. No.: 563,249

[22] Filed: Dec. 19, 1983

[30] Foreign Application Priority Data

Dec. 29, 1982 [JP] Japan .................. 57-234554

[51] Int. Cl.$^4$ ............................................. B01D 13/02
[52] U.S. Cl. ................................. 204/301; 204/299 R
[58] Field of Search ............................ 204/301, 299 R

[56] References Cited

U.S. PATENT DOCUMENTS

| | | | |
|---|---|---|---|
| 3,705,845 | 12/1972 | Everaerts | 204/299 R |
| 3,869,365 | 3/1975 | Sunden | 204/299 R |
| 3,948,753 | 4/1976 | Arlinger | 204/299 R |
| 3,998,719 | 12/1976 | Deml et al. | 204/180 R |
| 4,203,817 | 5/1980 | Schutt | 204/180.1 |
| 4,515,676 | 5/1985 | Kawai et al. | 204/299 R |

Primary Examiner—John F. Niebling
Assistant Examiner—B. J. Boggs, Jr.
Attorney, Agent, or Firm—Oblon, Fisher, Spivak, McClelland & Maier

[57] ABSTRACT

The disclosed invention relates to a cell unit for use in observing an electophoresis which utilizes a measurement cell which accommodates a liquid specimen. A pair of conduit elements are used to introduce and discharge the liquid specimen into and from the measurement cell with one of the conduit elements having a flexible tube portion. Also included is a pair of valves for closing a pair of conduit elements with at least one of the valves being utilized as a pinch valve to pinch the flexible tube. A pair of housing elements accommodate a pair of electrodes with the electrodes producing an electric potential gradient in the specimen. Lastly, a pair of diaphragm elements are each disposed between the measurement cell and one of the pair of housing elements in order to separate a space in the measurement cell from the space in the associated housing element. One of the pair of diaphragm elements is disposed in order to absorb a fluctuation of pressure in the liquid in a particular space defined by the pair of diaphragm elements and the valves in order to securely and easily seal the liquid specimen within the space defined by the pair of diaphragm elements and the valves. The device is also used to minimize the flow of liquid specimen within the measurement cell after sealing.

9 Claims, 10 Drawing Figures

CELL UNIT FOR OBSERVING ELECTROPHORESIS

BACKGROUND OF THE INVENTION

1. Field of the Invention

This invention is concerned with a cell unit for observing an electrophoresis, more particularly with a measurement or measuring cell unit for observing an electrophoresis of living cells by means of a microscope.

2. Description of the Prior Art

Apparatus adapted to measure the velocities of minute or fine particles such as living cells in a liquid specimen under the effect of an electric field and calculate the electrophoretic mobility of the particles have been well-known and generally referred to as a living cell electrophoresis apparatus or electrophoretic apparatus for living cells. Upon observing or measuring the velocities or the electrophoretic mobility or mobilities of the particles in the liquid specimen flow or turbulence of the liquid specimen which affects the movement of particles to cause errors in observed or measured values has to be eliminated as much as possible.

In view of the above, the measurement cell system in the electrophoretic apparatus generally comprises a unit including a measurement cell, electrodes for giving the electric potential gradient to the liquid specimen in the measurement cell, diaphragms formed by substantially rigidly supported membranes, valves for sealing the specimen in the measurement cell (hereinafter referred to as sealing valves) and so on. The diaphragm formed by the substantially rigidly supported membrane serves for preventing the gas or bubbles produced at surfaces of the electrodes in the course of the electrode reaction from entering the measurement cell. The diaphragm is made of a substantially rigidly supported porous membrane such as an ion-exchange membrane or a dialysis membrane and, in conventional measurement cell units, have been designed to be secured by an adequate means such as a perforated plate so that they may not be bent nor displaced. Each of the sealing valves which are disposed in ducts as conduits for introducing and discharging the liquid specimen into and from the measurement cell generally comprises a cock made of glass, or a sluice valve made from teflon (polytetrafluoroethylene). In the measurement of the velocities of the particles in the liquid specimen in the electric field by using the measurement cell unit of this type, the stability or reproducibility of the measurement is largely dependent on the way of sealing or confining the liquid specimen in the measurement cell. Accordingly, those valves having a good sealing performance and not causing the flow or turbulence of the liquid specimen to be sealed upon closing operation of the valves have been demanded for as the sealing or confining valve for use in the measurement cell unit for electrophoresis. In this viewpoint, a pinch valve or a pinch cock designed to nip or pinch a flexible or resilient tube to close the liquid passage in the tube has been considered unsuitable for the sealing valve, because it deforms the flexible tube upon pinching to affect the liquid specimen to be sealed, that is, it causes the undesired flow or turbulence of the liquid specimen due to the change in the inner pressure of the tube upon sealing or confining the liquid specimen in a limited space including the space in the measurement cell.

Although the conventional valve such as the glass cock and the teflon sluice valve do not cause the sealed liquid specimen to move or flow, the sealing performances of these valves are not adequate but the sealing performance or degree of the sealing of the valves fluctuates on varies on every opening and closing operation of the valves, and thus desired stability can not always be obtained in the measurements or observations of the living cell electrophoresis.

In order to overcome the foregoing problems cause by the conventionally used valves in the measurement cell unit, the inventors have chosen a pinch valve having a good sealing performance as the sealing valve while making an attempt to solve the problem of the flow of the liquid specimen attributable to the use of the pinch valve by the improvement in other part of the cell unit.

SUMMARY OF THE INVENTION

The object of this invention is to provide a measurement cell unit for observing electrophoresis in which a liquid specimen can be sealed in a predetermined space easily and adequately and the flow of the liquid specimen in the measuring cell upon sealing can be minimized.

The above object can be attained in accordance with this invention by a cell unit for observing an electrophoresis having the following elements;

a measurement cell for accomodating a liquid specimen therein;

a pair of conduit means for introducing and discharging the liquid specimen into and from the measurement cell therethrough, at least one of the conduit means having a portion made of a flexible tube;

a pair of valve means, each valve means being adapted to close a respective one of the pair of conduit means, at least one of the valve means associated with said at least one of the conduit means being in the form of a pinch valve adapted to be able to pinch the flexible tube;

a pair of housing means for accomodating a pair of electrodes therein, the pair of electrodes being adapted to produce an electric potential gradient in the liquid specimen within the measurement cell;

a pair of diaphragm means, each being disposed at a position between the measurement cell and a respective one of the pair of housing means so as to separate a space in the measurement cell from a space in the respective one of the housing means, at least one of the pair of diaphragm means being disposed displaceably so as to absorb a fluctuation of a pressure of the liquid specimen in a space defined by the pair of diaphragm means and valve means.

In the measurement cell unit according to this invention, it is preferred that both of the pair of conduit means have portions made of flexible tubes, both of the pair of valve means are in the form of pinch valves adapted to be able to pinch the flexible tube, and both of the pair of diaphragm means are disposed displaceably so as to absorb the fluctuation of the pressure of the liquid specimen in the space defined by the pair of diaphragm means and valve means.

The measurement cell is made of an optically transparent material so as to allow the observation of the electrophoretic behavior of the charged particles in the liquid specimen by means of the microscope.

One of the features of this invention is to use a flexible or resilient polymeric material as the conduit means or duct for introducing and/or discharging the liquid specimen into and/or from the measurement cell and to use the pinch valve as the sealing valve.

Another feature of this invention is to dispose the diaphragm displaceably so that the fluctuation of the pressure can be suppressed or absorbed in the space defined by the diaphragms and the pinch valves.

A preferred embodiment of the measurement cell unit according to this invention is adapted to absorb, the undesirable effect of the pinch valve on the liquid specimen by utilizing the bending displacement of the flexible diaphragm or partition membrane which allows some ion to pass therethrough. Specifically, the flexible diaphragm or partition membrane used in this invention may be designed as a so-called mechanical diaphragm in which the membrane is not secured as in the conventional cell unit, for example, by a perforated plate or the like, but freely displaceable depending on the fluctuation in the pressure of the liquid specimen.

Alternatively, the diaphragm can be made displaceable by securing the peripheral part thereof displaceably to a conduit which is connected to the measurement cell unit by way of a separate flexible membrane or bellows. Furthermore, a piston-like member slidably fitted into the conduit of a cylinder-like tube situated between the measurement cell unit and the electrode housing may be formed with an opening at the end face thereof and a partition membrane may be secured to the end face at a peripheral portion thereof so as to cover the opening.

BRIEF DESCRIPTION OF THE DRAWINGS

This invention is to be described in more details referring to the accompanying drawings, by which the foregoing and other objects, as well as the features of this invention will be made clearer in which.

DETAILED DESCRIPTION OF THE PREFERRED EMBODIMENTS

Figure 1:
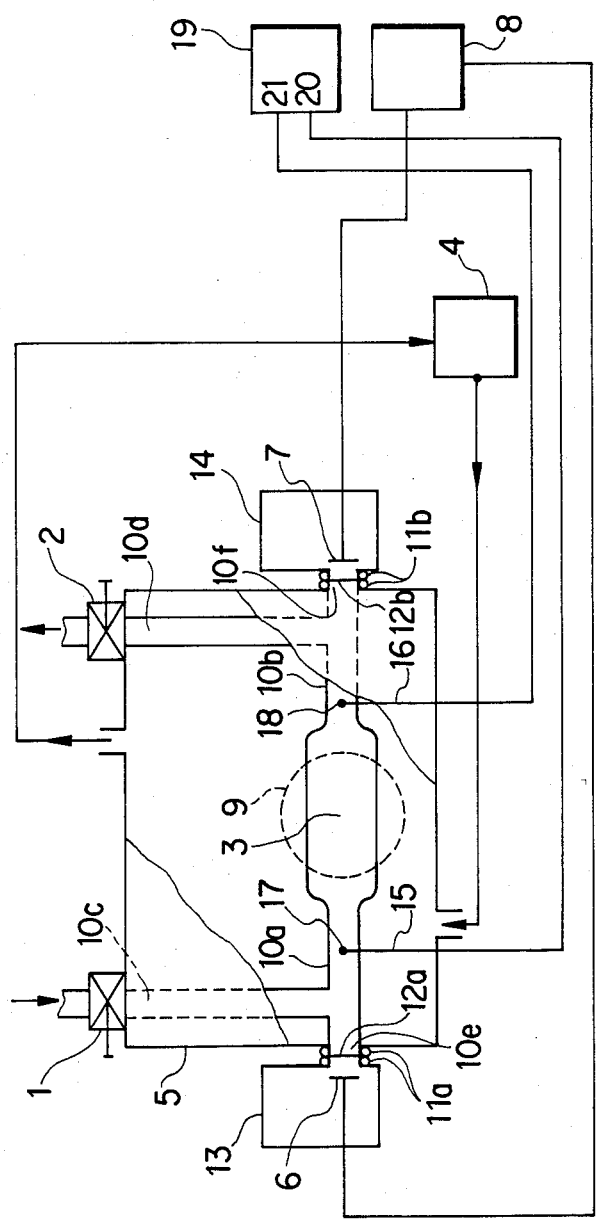
FIG. 1 is an illustrative view showing the entire part of an electrophoresis apparatus including a cell unit for observing electrophoresis.

Referring now to the drawings, wherein like reference numerals designate identical or corresponding parts throughout the several views, and more particularly to FIG. 1 schematically shows an example of an apparatus for observing electrophoresis by means of the microscope. In carrying out the measurement by the electrophoretic apparatus, a liquid specimen is introduced or supplied through an opened sealing valve 1 or 2 into an optically transparent measurement cell 3. The measurement cell 3 is kept at a constant temperature within a thermostat bath 5 externally equipped with a temperature control mechanism 4 for maintaining the temperature at a predetermined level. After supplying the liquid specimen, the sealing valves 1 and 2 are closed and an electric field or electric potential gradient is applied to the liquid specimen in the measurement cell 3 by a DC constant-current power supply 8 through a pair of electrodes 6 and 7 disposed on both sides of the measurement cell 3. The liquid specimen or the charged particles in the liquid in the measurement cell 3 is moved by the electric field thus applied or the electric potential gradient thus produced and the velocities of the specimen or of the charged particles in the liquid is observed or measured by means of the microscope through a view window 9. After the measurement, the liquid specimen is discharged from the opened sealing valve 1 or 2. The measurement cell 3 has glass tubes 10a, 10b on its both ends. The glass tubes 10a, 10b are connected to the sealing valves 1 and 2 respectively at their one ends 10c, 10d. Branched open ends 10e, 10f of the glass tubes 10a, 10b are connected respectively by way of gaskets 11a, 11b and diaphragms 12a, 12b to electrolyte baths or electrode housings 13, 14 accomodating the electrodes 6, 7 and electrolytes therein. Electrodes 15, 16 made of platinum for voltage measurement are protruded at their top ends 17, 18 into the passages in the glass tubes 10a, 10b, and are electrically connected to input terminals 20, 21 of a voltmeter 19.

Figure 2:
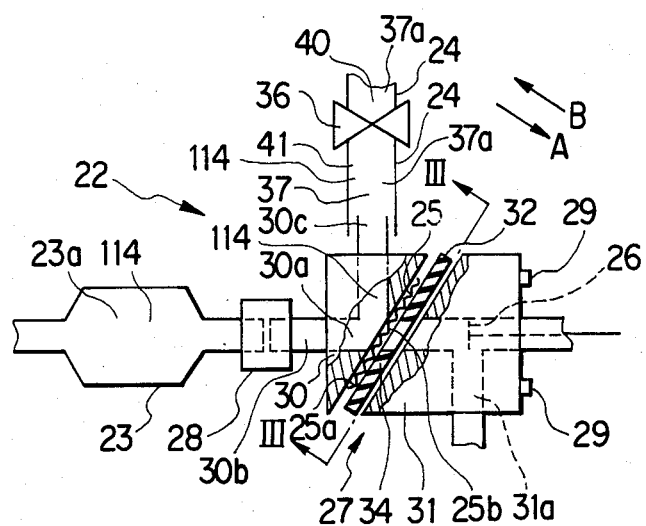
FIG. 2 is a partially broken illustrative view for a part of the cell unit for observing electrophoresis as a preferred embodiment according to this invention.

FIG. 2 is a schematic view of a part of a cell unit for observing electrophoresis 22 according to this invention. A measurement cell 23 is connected to a flexible tube 24 and coupled with an electrode 26 similar to the electrode 7 for applying electric field to the liquid specimen in the cell 23 through a diaphragm 25 which allows the electric current to pass therethrough.

In the actual embodiment of the cell unit 22, the similar or same components are symmetrically provided at the left-hand side of the measurement cell 23 with the components at the right-hand side of the measurement cell 23 shown in FIG. 2 just like the measurement cell unit in FIG. 1, that is another flexible tube similar to the tube 24, another diaphragm similar to the diaphragm 25, another electrode similar to the electrode 26, etc. are also provided at the left-hand side of the cell 23 of FIG. 2, but the explanation will be made only to the right-hand part of the cell 23 for the sake of the simplicity.

In a block 27 whose passage 30a is liquid-tightly connected to a space 23a in the cell 23 through a packing 28 at a tube portion 30b shown in the FIG. 2, the diaphragm or partition membrane 25 is held at a peripheral portion 25a thereof in a liquid and air-tight manner through a gasket 32 between sub-blocks 30 and 31 integrally secured with each other by means of screws 29 at an outside position of a corner of the passage 30a from a valve 36 to the cell 23 where the passage 30a is bent. The gasket 32 has an opening 33 for allowing a central portion 25b of the diaphragm 25 to be displaced in the direction A or B, and supports the outer peripheral edge 25a of the partition membrane 25 at the peripheral edge 34 of the opening 33. The gasket 32 is formed with apertures 35 for insertion of the screws 29. The subblock 31 serves for the electrode housing accomodating the electrode 26 and electrolyte in its chamber or space 31a which is separated from the passage 30b and the space or chamber 23a by the diaphragm 25a, and is substantially kept at an atmospheric pressure. A pinch valve generally represented by the reference numeral 36 seals or confines the liquid specimen in the measurement cell 23 by pinching or nipping the flexible tube 24 which is liquid-tightly connected to the tube portion 30c of the subblock 30.

Figure 4:
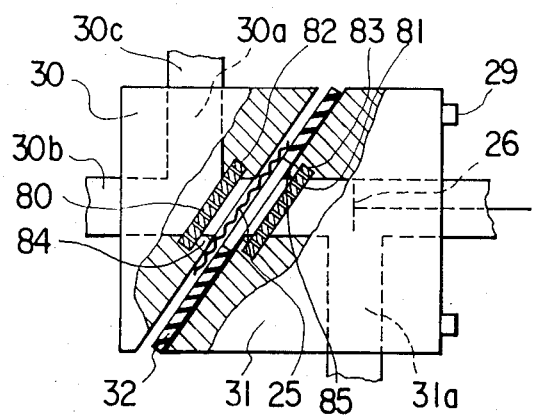
FIG. 4 is a partially broken explanatory view of a modification of a portion around the diaphragm.
Figure 5:
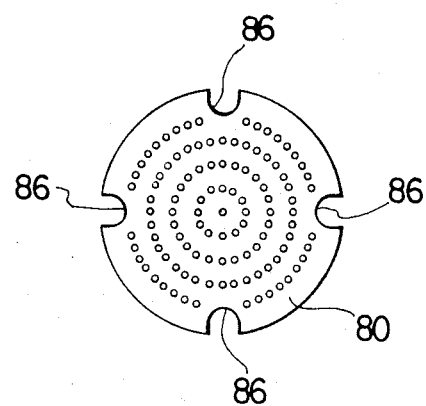
FIG. 5 is an explanatory plan view of a perforated plate of FIG. 4.

The diaphragm or partition membrane 25 is constituted as a mechanical diaphragm freely displaceable at the free central part 25b in the direction A or B by the conventional method using the gasket 32 composed of a flat packing, O-ring or the like so as to support only the peripheral portion 25a of the diaphragm 25. As a modification of this embodiment, it is preferred in view of the life of the diaphragm 25 to dispose perforated plates 80, 81 spaced apart on both sides of the diaphragm 25 as shown in FIG. 4, so that the partition membrane may be supported on and protected by the perforated plates 80, 81 against a large fluctuation in the flow or pressure of the liquid specimen upon introduction and discharge of the specimen and the partition membrane can be displaced freely upon sealing. In the modification of FIG. 4, the circular perforated plates 80, 81 can be disposed in circular recesses 82, 83 formed the subblocks 30, 31 and supported by protruding portions 84, 85. The circular perforated plates 80, 81 can have cut-out portions 86 for enabling to mount or dismount the circular perforated plates 80, 81 into or from the circular recesses 82, 83 through protruding portions 84, 85 as shown in FIG. 5.

Figure 3:
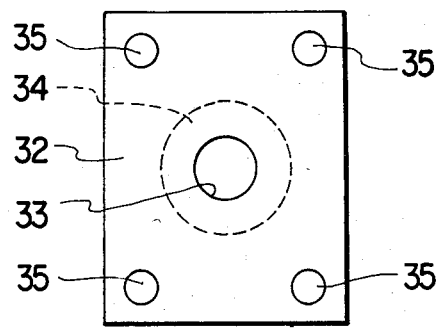
FIG. 3 is an illustrative view viewed along the line III—III in FIG. 2.
Figure 6:
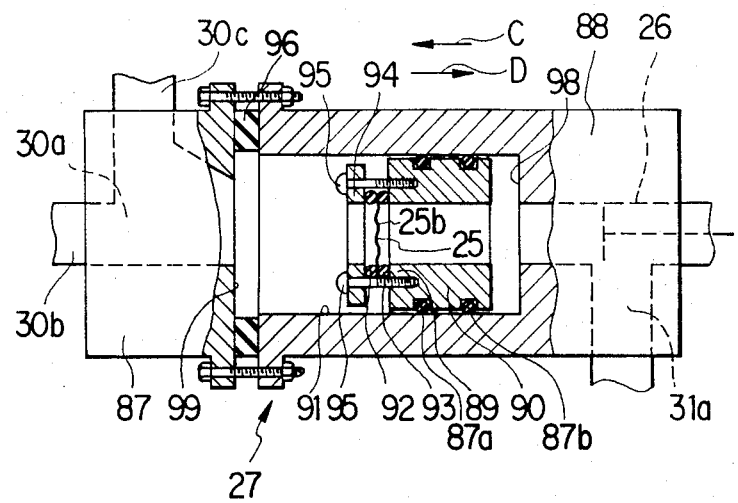
FIG. 6 is a partially broken explanatory view of a further modification of a portion around the diaphragm.
Figure 7:
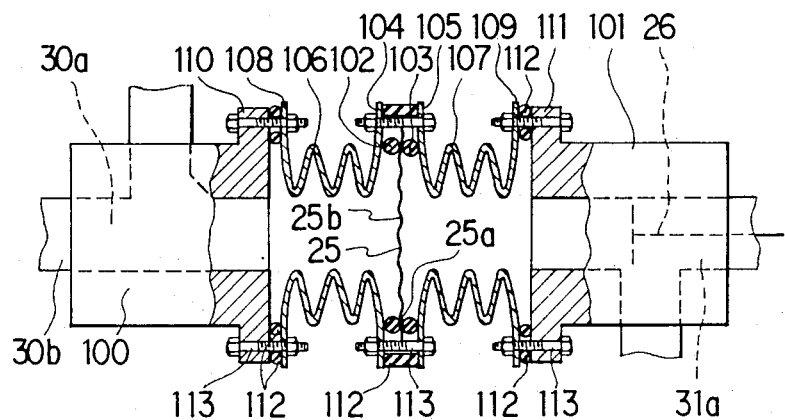
FIG. 7 is a partially broken explanatory view of a still further modification of a portion around the diaphragm.

The diaphragm 25 may be linearly displaced as a whole as shown in FIGS. 6 or 7 where components substantially identical with the components in FIG. 3 are represented by the same reference numeral.

In the modification shown in the FIG. 6, the block 27 comprises subblocks 87 and 88 similar to the subblocks 30, 31 respectively, and the diaphragm 25 is fixed to one end 89 of an annular piston-like member 90, which is fitted slidably in the directions C, D in an enlarged cylindrical bore 91 of the subblock 88, by means of sealing rings 92, 93, an annular retainer member 94 and screws 95. The subblock 87 is liquid-tightly connected to the subblock 88 through sealing ring 96. The end face 99 of the subblock 87 and the end face 98 of the bore 91 serve for restricting the displacement of the piston-like member 90 in the direction D, C respectively. References 87a, 87b are sealing rings.

In the other modification shown in the FIG. 7, the block 27 comprises subblocks 100 and 101, and the diaphragm 25 is supported at its peripheral 25a through sealing rings or gaskets 102, 103 between one annular ends 104, 105 of two generally hollow cylindrical bellows 106, 107 whose other ends 108, 109 are fixed to the flanged ends 110, 111 of the subblocks 100, 101 respectively. Reference numeral 112 represents a sealing ring for liquid-tight seal and reference numeral 113 represents securing means such as a screw and nut.

It will be apparent that the diaphragm 25 can be generally freely displaced in the directions C, D as a whole according to the displacement of the pistion-like member 90 or to the expansion or contraction of the bellows 106, 107 and that the free central portion 25b of the diaphragm 25 can be displaced in the directions C, D by being bent.

The diaphragm 25 may be made of a dialysis membrane, an ion exchange membrane or other membrane which has been conventionally employed in the cell unit for observing the electrophoresis. The membrane or diaphragm area is usually less than 100 mm$^2$ and, preferably, within a range between 50–3 mm$^2$ although it may be varied depending on the thickness of the membrane. The membrane area is related with two factors of the diaphragm 25, that is, the performance or function and the strength of the diaphragm.

In a case where the pressure of the liquid specimen increases or decreases in the space 37 within the flexible tube 24 communicated with the spaces 30a, 23a, for instance, the diaphragm 25 is displaced in the direction A(D) or B(C) respectively and enables to suppress or prevent the pressure fluctuation in the liquid specimen within the space 37 from propagating to the liquid specimen within the measurement cell 23 at least due to the distortion at the central part 25b thereof in the direction A or B depending on the pressure fluctuation, that is, the diaphragm 25 absorbs the pressure fluctuation or change.

Figure 8:
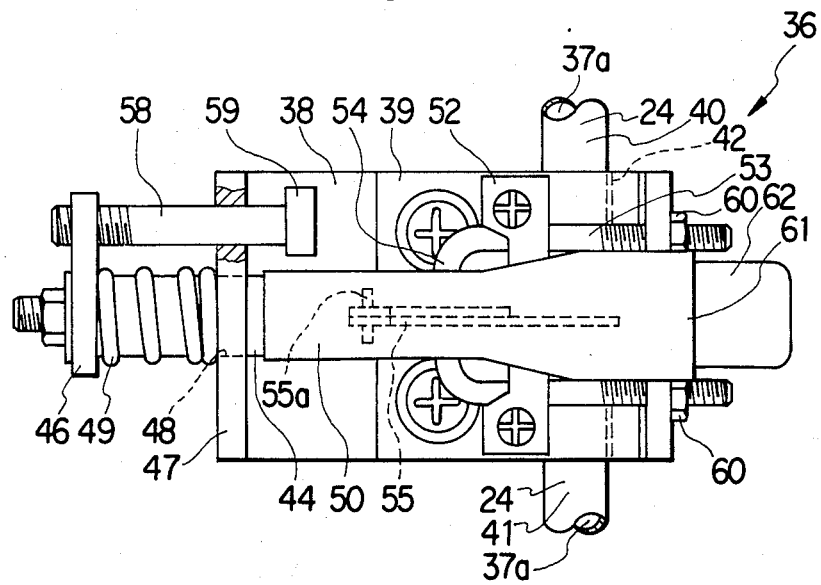
FIG. 8 and FIG. 9 are respectively partially broken explanatory plan view and front view of the pinch valve shown in FIG. 2.
Figure 9:
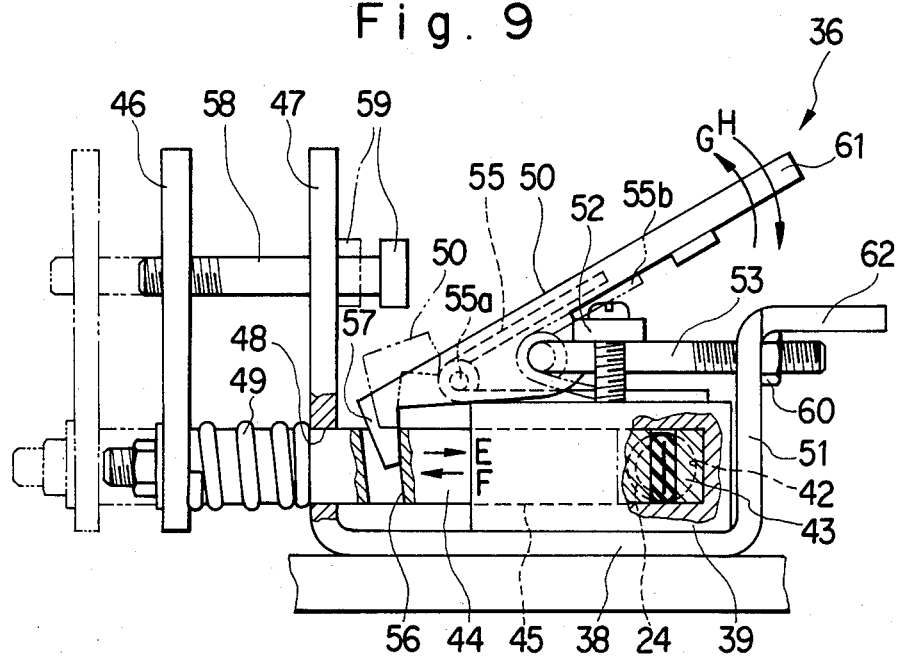

A pinch valve of a structure, for example, as shown in FIGS. 8 and 9 is used as the pinch valve 36, but other known pinch valves such as those generally referred to as a pinch cock may be used.

The pinch valve 36 shown in FIGS. 8 and 9 comprises a frame member 38 and a valve body 39 secured to the frame member 38. The valve body 39 has an aperture 42 for passing therethrough a flexible or resilient tube 24 composed of integral flexible or resilient tubular parts 40, 41 and also has a cylindrical hole 45 containing, fitted therein, a stationary pinching or nipping member 43 in the form of a semi- or partial cylinder and a plunger-like pinching or nipping member 44 movable in the direction E or F perpendicular to the extending direction of the aperture 42.

A grip wall member 46 is secured opposing to a wall portion 47 of the frame member 39 at the protruded end of the nipping member 44 passing through an aperture 48 in the grip wall portion 47. A spring 49 is mounted between the grip wall portion 47 and the grip wall member 46 for biasing the grip wall member 46 in the direction F apart from the grip wall portion 47. A stop member 50 adapted to stop the nipping member 44 is made pivotable around a shaft part 54 of a U-shaped pivot shaft member 53 supported by a protruding wall portion 51 of the frame member 38 and a retainer member 52 secured to the valve body 39 in the direction G or H while biased by a spring 55 in the direction G by a spring 55 which is supported by a pin 55a disposed in a recess of the stop member 50. Instead of mounting the spring 55 around the pin 55a, the spring 55b shown in FIG. 9 by imaginary lines may be mounted around the shaft part 54 of the U-shaped member 53 so as to bias the stop member 50 in the direction G if desired, for example, in the case where it is difficult to form a space or recess for mounting the pin 55a and the spring 55 in the stop member 50 because of its small size. When the nipping member 44 is displaced in the direction E till a position at which a liquid passage in the tube 24 can be closed completely by the combined action of the nipping member 44 and the stationary nipping member 43, the stop member 50 can be engaged at its engaging portion 57 with an inclined hole 56 formed at the intermediate part of the nipping member 44 so as to stop the displacement of the nipping member 44 in the direction F.

Reference numeral 58 represents a guide member for guiding the nipping member 44 in the direction E or F, reference numeral 59 represents a stop member for restricting the displacement of the nipping or seizing member 44 in the direction F within an appropriate range and reference numeral 60 represents a nut for adjusting the position of the shaft part 54 in the direction E or F.

By the use of the pinch valve 36, the passage 37a in the flexible or resilient tube 24 can be closed completely, for instance, by merely gripping the grip wall members 46 and 47 between fingers so as to bring them closer to each other against expansion of the spring 49 and the closed passage 37a in the flexible tube 24 can be opened, for example, by gripping the two end parts 61, 62 between fingers so as to bring them closer to each other because the engagement between the engaging portion 57 and hole 56 can be released allowing the nipping member to be displaced in the direction F by the spring 49.

In a case where the liquid specimen within the measurement cell 23 is sealed by the complete closure of the passage 37a in the tube 24 by means of the pinch valve 36, there have been usually a fear that the pressure of the liquid specimen within the space 114 consisting of the spaces 23a, 30a, 37 etc. defined by the valve 36, the similar valve at the left-hand side of the cell 23, the diaphragm 25 and the similar diaphragm at the left-hand side of the cell 23 may be increased when, after the closure of the passage 37a in the tube 24 by the nipping of the tube 24, the tube 24 is further seized or nipped to deform elastically so that the liquid specimen may be sealed completely at the closed part. However, since such a rise in the pressure can be actually or substantially absorbed by the distortion of the diaphragm or partition membrane 25 in the direction A or D according to this invention, the fear of the generation of the flow of the liquid specimen in the measurement cell 23 due to the closure of the pinch valve 36 can be minimized.

This invention is to be described hereinafter referring to an example which was actually carried out.

EXAMPLE AND COMPARATIVE EXAMPLE

Figure 10:
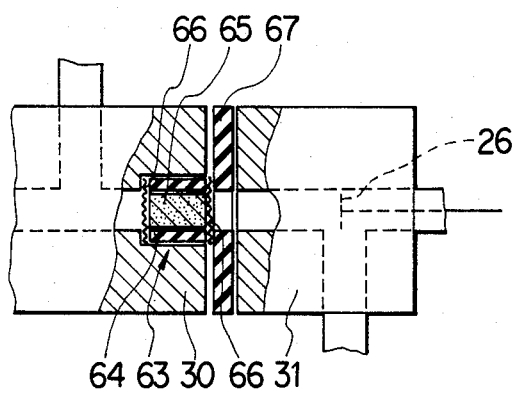
FIG. 10 is a partially broken illustrative view showing a rigidly supported state of the diaphragm formed by the substantially rigidly supported membrane in the conventional measurement cell unit.

The conventional cell unit for observing electrophoresis having the fixed diaphragm shown in FIG. 10 and the cell unit for observing electrophoresis according to this invention shown in FIG. 2 were used as the cell units for the electrophoretic apparatus shown in FIG. 1 so as to observe and measure the mobilities of a liquid specimen according to the conventional procedures and the reproducibilities in the observed (measured) value of mobilities by both of the measurement cell units were examined or compared. In the meantime, FIG. 10 shows a perforated plate 63 composed of a teflon ring 64 inserted with a porous glass product 65, a gasket 67, and diaphragm 66 formed by a membrane substantially rigidly supported between the perforated plate 63 and the gasket 67.

Conditions for the measurement were as follows:
Specimen whose electrophoretic mobility was measured:
  erythrocyte of a sheep
Suspension medium:
  phosphate buffered saline of pH 7.2
Electric current flow through the measurement cell:
  10 mA
Measurement cell:
  rectangular parallelopiped type (cross sectional space area 0.7 mm×7 mm)

A cation exchange membrane (0.3 mm thickness, 25 mm$^2$ membrane area) was used as the diaphragm and the pinch valve shown in FIGS. 8 and 9 was used as the sealing valve.

Measurement was carried out twice by reversing the orientation of the electric field or polarities of the electrodes 6, 7 and the data showing the difference within 10% between the rightward and leftward velocities were employed judging that the operating condition of each measurement cell unit was stable during the measuring period.

The mobility ($\mu$m/sec/volt/cm) was measured for each of 50 erythrocyte cells in one liquid specimen and the mean value for the 50 cells was determined as the mobility of the specimen. Such measurement was repeated for 20 times to determine the standard deviation of the mobility of the specimen, in which the standard deviation was within 1–2% in a case of using the cell unit according to this invention, whereas it was 3–4% in the conventional cell unit employing the diaphragm formed by the substantially rigidly supported membrane shown in FIG. 10.

From the result of the experiment, it is apparent that the stability of the measurement can be significantly improved according to this invention.

Obviously, numerous modifications and variations of the present invention are possible in light of the above teachings. It is therefore to be understood that within the scope of the appended claims the invention may be practiced otherwise than as specifically described herein.

What is claimed is:

1. A cell unit for observing an electrophoresis comprising:
    measurement cell for accommodating a liquid specimen therein;
    a pair of conduit means for introducing and discharging the liquid specimen into and from the measurement cell therethrough, both of the pair of the conduit means having portions made of flexible tubes;
    a pair of valve means, each valve means being adapted to close a respective one of the pair of conduit means, and both of the pair of the valve means associated with both of the conduit means being in the form of pinch valves adapted to be able to pinch the flexible tubes;
    a pair of housing means for accommodating a pair of electrodes therein, the pair of electrodes being adapted to produce an electric potential gradient in the liquid specimen within the measurement cell; and
    a pair of diaphragm means, each being disposed at a position between the measurement cell and a respective one of the pair of housing means so as to separate a space in the measurement cell from a space in the respective one of the housing means, both of the pair of diaphragm means being disposed displaceably so as to absorb a fluctuation of a pressure of the liquid specimen in a space defined by the pair of diaphragm means and valve means, each of the diaphragm means being supported liquidtightly at a peripheral portion thereof, the central portion of each diaphragm means being displaceable in a direction perpendicular to a plane of said each diaphragm means with respect to the peripheral portion of said each diaphragm, and at least one of the diaphragm means being supported linearly movably as a whole.

2. The cell unit according to claim 1, wherein the linearly movable diaphragm is fixed liquid-tightly to one end of a hollow cylindrical piston-like member slidably mounted in a cylindrical passage between the measurement cell and the electrode housing means.

3. The cell unit according to claim 1, wherein the linearly movable diaphragm is supported liquid-tightly between one ends of two bellows, the other end of one of the bellows being connected liquid-tightly to the conduit means, and the other end of another bellows being connected liquid-tightly to the electrode housing means.

4. A cell unit for observing an electrophoretic mobility comprising:
   a measurement cell for accommodating a liquid specimen therein;
   a pair of conduit means for introducing and discharging the liquid specimen into and from the measurement cell therethrough, at least one of the conduit means having a portion made of a flexible tube;
   a pair of valve means, each valve means being adapted to close a respective one of the pair of conduit means, and at least one of the valve means associated with said at least one of the conduit means being in the form of a pinch valve adapted to be able to pinch the flexible tube;
   a pair of housing means for accommodating a pair of electrodes therein, the pair of electrodes being adapted to produce an electric potential gradient in the liquid specimen with the measurement cell; and
   a pair of diaphragm means, each being disposed at a position between the measurement cell and a respective one of the pair of housing means so as to separate a space in the measurement cell from a space in the respective one of the housing means, and at least one of the pair of diaphragm means being disposed displaceably so as to absorb a fluctuation of a pressure of the liquid specimen in a space defined by the pair of diaphragm means and valve means wherein at least one of said disphragm means is supported linearly movably as a whole.

5. The cell unit according to claim 4, wherein both of the pair of conduit means have portions made of flexible tubes,
   both of the pair of valve means are in the form of pinch valves adapted to be able to pinch the flexible tubes, and
   both of the pair of diaphragm means are disposed displaceably so as to absorb the fluctuation of the pressure of the liquid specimen in the space defined by the pair of diaphragm means and valve means.

6. The cell unit according to claim 5, wherein each of the diaphragm means is supported liquid-tightly at a peripheral portion thereof, the central portion of each diaphragm means being displaceable in a direction perpendicular to a plane of said each diaphragm means with respect to the peripheral portion of said each diaphragm means.

7. The cell unit according to claim 6, wherein each diaphragm means is disposed at an outside position of a corner of the respective conduit means where the conduit means from the valve means to the measurement cell is bent.

8. The cell unit according to claim 6, wherein at least one of the diaphragm means is supported stationarily at the peripheral portion thereof with respect to the measurement cell.

9. The cell unit according to claim 8, wherein means for restricting the displacement of the central portion of the diaphragm means having the stationary peripheral portion are provided.

* * * * *